US00PP16095P3

(12) United States Plant Patent
Trees

(10) Patent No.: US PP16,095 P3
(45) Date of Patent: Nov. 8, 2005

(54) ***LANTANA* PLANT NAMED 'BALANDGOLD'**

(50) Latin Name: *Lantana camara*
Varietal Denomination: Balandgold

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 96 days.

(21) Appl. No.: 10/741,011

(22) Filed: Dec. 19, 2003

(65) Prior Publication Data

US 2005/0138710 P1 Jun. 23, 2005

(51) Int. Cl.[7] ..... A01H 5/00

(52) U.S. Cl. ..... Plt./227

(58) Field of Search ..... Plt./227

*Primary Examiner*—Kent Bell

(74) *Attorney, Agent, or Firm*—Wood, Phillips, Katz, Clark & Mortimer

(57) ABSTRACT

A new and distinct *Lantana* plant named 'Balandgold' characterized by its bright yellow-colored flowers, dark green-colored foliage, and upright and mounded growth habit.

1 Drawing Sheet

Latin name of genus and species of plant claimed: *Lantana camara.*

Variety denomination: 'Balandgold'.

BACKGROUND OF THE INVENTION

The present invention relates to a new and distinct cultivar of *Lantana* plant botanically known as *Lantana camara* and hereinafter referred to by the cultivar name 'Balandgold'.

The new cultivar was developed by the inventor in a controlled breeding program during January 2000, at Arroyo Grande, Calif. The objective of the breeding program was the development of *Lantana* cultivars with a well-branched, compact habit, continuous flowering and dark green foliage.

The new cultivar was the product of the open pollination of the commercially available *Lantana* cultivar New Gold (not patented) characterized by its gold-colored flowers, medium green-colored foliage, and compact upright growth habit. The new cultivar was selected in February 2001 as a single flowering plant within the progeny of the above stated open-pollination and was initially designated '471-5'.

Asexual reproduction of the new cultivar by terminal stem cuttings taken since February 2001 at Arroyo Grande, Calif. and West Chicago, Ill. has demonstrated that the new cultivar reproduces true to type, with all the characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any variance in genotype.

It was repeatedly found that the cultivar of the present invention:

1. Exhibits bright yellow-colored flowers,
2. Forms dark green-colored foliage, and
3. Exhibits an upright and mounded growth habit.

Plants of the new cultivar differ from plants of the female parent primarily in foliage size, foliage color and growth habit.

Of the many *Lantana* cultivars known to the inventor, the closest to the new cultivar is Goldsonne (not patented). However, in a side-by-side comparison, at West Chicago, Ill., plants of the new cultivar differed from plants of 'Goldsonne' in the following characteristics:

1. Plants of the new cultivar have smaller inflorescences than plants of 'Goldsonne', and
2. Plants of the new cultivar have flowers of a darker yellow color than 'Goldsonne'.

BRIEF DESCRIPTION OF THE PHOTOGRAPHS

The accompanying photographs show as nearly true as it is reasonably possible to make the same in color illustrations of this type, typical flower and foliage characteristics of the new cultivar. Colors in the photographs differ slightly from the color values cited in the detailed description, which accurately describes the colors of 'Balandgold'. The plants were grown for 10 weeks in a greenhouse at West Chicago, Ill.

DETAILED BOTANICAL DESCRIPTION

Figure 1:
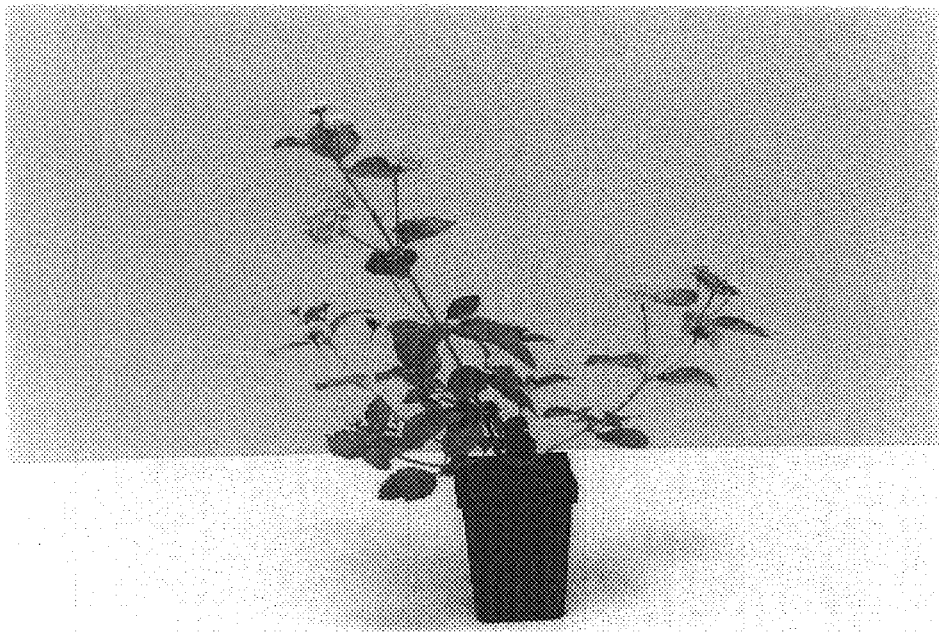
FIG. 1 illustrates a side view of the overall growth and flowering habit of 'Balandgold'.
Figure 2:
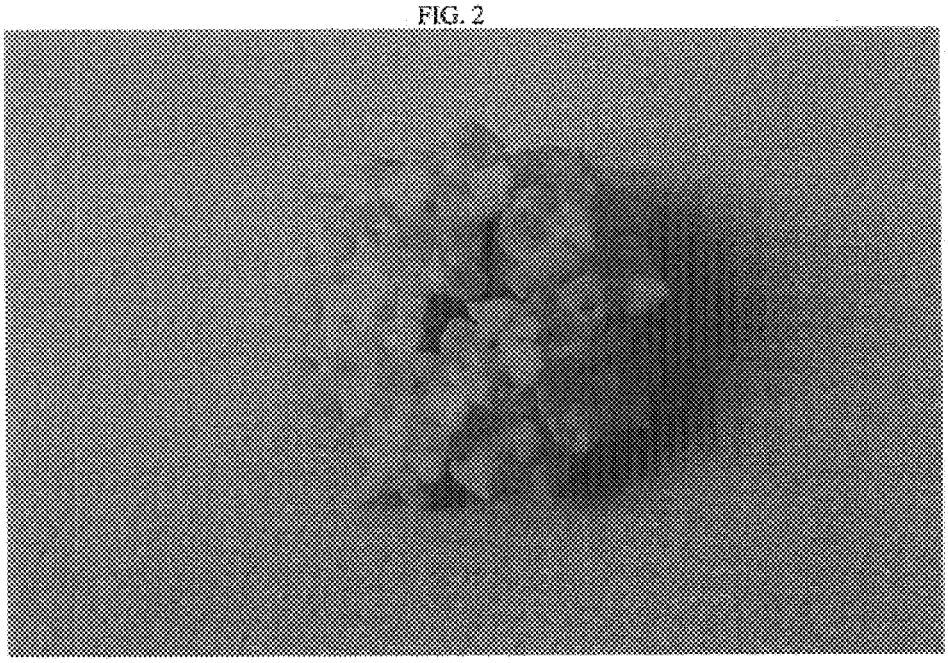
FIG. 2 illustrates a close-up view of a single inflorescence of 'Balandgold'.

The chart used in the identification of colors described herein is The R.H.S. Colour Chart of The Royal Horticultural Society, London, England, 1995 edition, except where general color terms of ordinary significance are used. The color values were determined on Jul. 25, 2003. The readings were taken between 9:00 and 11:00 a.m. under natural daylight conditions. The plants were produced from terminal stem cuttings taken from stock plants and were grown in a double polycarbonate-covered greenhouse at West Chicago, Ill. under conditions comparable to those used in commercial practice. The plants were grown in 10 cm pots for 10 weeks while utilizing a soilless growth medium. Greenhouse temperatures were maintained at approximately 75°–85° F. (24°–29° C.) during the day and approximately 62°–68° F. (17°–20° C.) during the night. Greenhouse light levels were maintained at 4,000–10,000 footcandles during the day.

Botanical classification: *Lantana camara* cultivar 'Balandgold'.

Parentage: Open pollination of the cultivar New Gold, not patented.

Propagation:

*Type cutting.*—Terminal stem.

*Time to initiate roots.*—Approximately 7 to 11 days.

*Time to develop roots.*—Approximately 4 weeks.

*Root description.*—Fine, fibrous.

*Rooting habit.*—Freely branching.

Plant description:

*Habit of growth.*—Vigorous. Forms lateral branches at every node. Pinching enhances basal branching. A mature plant, 10 weeks after the planting of a rooted cutting, measures approximately 29.3 cm in height from soil level to top of plant plane and approximately 44.8 cm in diameter (area of spread) with 1.7 main branches.

*Form.*—Upright, mounded and spreading.

*Branch.*—Shape: Quadrilateral. Strength: Strong. Length: Approximately 37.4 cm. Diameter: Approximately 3.2 mm. Texture: Moderately pubescent with short stiff hairs. Color of young supple branch: 146C. Color of mature woody branch: N199A. Internode length at middle of stem: Approximately 7 cm.

*Foliage.*—Type: Simple. Arrangement: Opposite. Orientation to stem: Perdendicular. Fragrance: Faint, spicy. Shape: Ovate. Margin: Crenate. Apex: Acute. Base: Cuneate. Texture of upper surface: Moderately pubescent. Texture of lower surface: Densely covered with short, stiff hairs. Leaf length: Approximately 6.9 cm. Leaf width: Approximately 5 cm. Venation pattern: Pinnate. Color of upper surface of mature foliage: Closest to 139A with veins of 145C. Color of lower surface of mature foliage: 137C with veins of 145C. Petiole length: Approximately 1 cm. Petiole diameter: Approximately 2 mm. Petiole texture of upper surface: Sparsely covered with short, stiff hairs. Petiole texture of lower surface: Dense stiff hairs with moderate amount of glandular pubescence. Petiole color: Both surfaces: Closest to 145C.

Flowering description:

*Flowering habit.*—Freely flowering.

*Natural flowering season.*—Year round in greenhouse environment and spring through autumn in outdoor garden.

Inflorescence description:

*Type.*—Corymb.

*Shape.*—Spherical.

*Quantity per plant.*—Approximately 6.

*Size.*—Depth (height): Approximately 2 cm. Diameter: Approximately 3.7 cm. Number of flowers per inflorescence: Approximately 28 fully opened flowers at any one time. Each flower is subtended by a single bract.

*Bract.*—Shape: Lanceolate. Length: Approximately 6 mm. Width: Approximately 1 mm. Apex: Acute. Margin: entire. Texture: Lower surface is densely pubescent, upper surface is slightly pubescent with short hairs. Color of both surfaces: 137A.

*Peduncle.*—Shape: Quadrilateral. Length: Approximately 5.4 cm. Diameter: Approximately 1.4 mm. Aspect: At acute angle to branch. Texture: Pubescent with very short glandular hairs and moderate amount of short stiff hairs. Color: 146C.

Flower description:

*Type.*—Salverform.

*Fragrance.*—Light, sweet.

*Aspect.*—Concave.

*Lastingness of bloom.*—Approximately 7 days from first color on outer buds to last flower dropping.

*Bud.*—Shape: Roughly spherical. Length: Approximately 3 mm. Width: Approximately 3 mm. Color: 15A.

*Corolla size.*—Length: Approximately 1.1 cm. Width: Approximately 1 cm.

*Petals.*—Four, non imbricate, non-symetrical, fused at base forming corolla tube. Shape: Obovate. Margin: Entire. Texture of upper and lower surfaces: Glabrous. Length from throat: Approximately 5 mm. Petal color when first open: Upper surface: 17B. Lower surface: 15C. Petal color when fully open: Upper surface: 17B. Lower surface: 21B.

*Upper petal.*—Width: Approximately 4 mm. Apex: Obtuse.

*Lateral petal.*—Width: Approximately 5 mm. Apex: Cuspidate.

*Lower petal.*—Width: Approximately 4 mm. Apex: Obtuse.

*Corolla tube.*—Length: Approximately 1.2 cm. Diameter at tube opening: Approximately 1.5 mm. Diameter at base: Approximately 1 mm. Texture of outer surface: Densely covered with short hairs. Texture of inner surface: Glabrous except for hairs around opening. Color of both inner and outer surfaces: When first open: 15C. When fully open: 21B.

*Calyx.*—Shape: Tubular, formed by 5 fused sepals. Calyx length: Approximately 3 mm. Calyx diameter at apex: Approximately 1.8 mm. Sepal length: 3 mm. Sepal width: 1 mm. Sepal texture: Moderate pubescence. Sepal color: 145C.

*Reproductive organs.*—Stamens: Four per flower, fused (adnate) to the corolla tube. Filament: Length of free portion: Approximately 1 mm. Filament color: 5C. Anther shape: 2 lobed. Anther length: 0.9 mm. Anther color: 162A. Amount of pollen: Sparse. Pollen color: 4D. Pistil quantity: One per flower. Pistil length: 4 mm. Stigma shape: Oval. Stigma length: 0.5 mm. Stigma color is 144B. Style length: Approximately 2.5 mm. Style color: 144C. Ovary length: 1 mm. Ovary color: 144B.

Seed and fruit production: Neither seed nor fruit production has been observed.

Disease and pest resistance: Resistance to pathogens or pests common to *Lantana* has not been observed.

Hardiness zone: 'Balandgold' is hardy in zones nine (9) and above.

What is claimed is:

1. A new and distinct cultivar of *Lantana* plant named 'Balandgold' substantially, as herein shown and described, which:

1. Exhibits bright yellow-colored flowers,
2. Forms dark green-colored foliage, and
3. Exhibits an upright and mounded growth habit.

* * * * *